United States Patent [19]
Gordon et al.

[11] Patent Number: 5,256,692
[45] Date of Patent: Oct. 26, 1993

[54] SULFUR-CONTAINING HMG-COA REDUCTASE INHIBITORS

[75] Inventors: Eric M. Gordon, Pennington; Jelka Pluscec, Trenton, both of N.J.

[73] Assignee: E. R. Squibb & Sons, Inc., Princeton, N.J.

[21] Appl. No.: 817,875

[22] Filed: Jan. 7, 1992

[51] Int. Cl.$^5$ .................... A01N 37/10; C07C 317/00
[52] U.S. Cl. .................... 514/532; 514/570; 546/223; 548/323.5; 548/547; 560/11; 560/15; 562/426; 562/429
[58] Field of Search ............... 562/429, 426; 560/15, 560/11; 514/532, 570

[56] References Cited

U.S. PATENT DOCUMENTS

| | | | |
|---|---|---|---|
| 4,062,973 | 12/1977 | Nickl et al. ............... | 514/532 |
| 4,191,776 | 3/1980 | Nickl et al. ............... | 514/532 |
| 5,001,128 | 3/1991 | Neuenschwander et al. ...... | 514/570 |
| 5,025,000 | 6/1991 | Karanewsky et al. ............ | 514/80 |
| 5,025,017 | 6/1991 | Karanewsky et al. ............ | 514/277 |
| 5,049,577 | 9/1991 | Varma et al. ............... | 514/409 |
| 5,049,578 | 9/1991 | Varma et al. ............... | 514/409 |
| 5,089,523 | 2/1992 | Varma et al. ............... | 514/460 |
| 5,091,378 | 2/1992 | Karanewsky et al. ............ | 514/80 |
| 5,099,035 | 3/1992 | Saunders et al. ............... | 549/292 |

FOREIGN PATENT DOCUMENTS

| | | |
|---|---|---|
| 0127848 | 12/1984 | European Pat. Off. . |
| 2205838 | 12/1988 | United Kingdom . |
| PCT8603488 | 6/1986 | World Int. Prop. O. . |

*Primary Examiner*—José G. Dees
*Assistant Examiner*—Dwayne C. Jones
*Attorney, Agent, or Firm*—John M. Kilcoyne

[57] ABSTRACT

Novel sulfur-containing compounds which inhibit the activity of 3-hydroxy-3-methylglutaryl-coenzyme A (HMG-CoA) reductase, having a sulfur-containing side-chain bonded to a hydrophobic anchor group through an acetylenic or ethylenic linkage. Pharmaceutical compositions, and methods of use for the treatment or prevention of hypercholesterolemia, atherosclerosis, hyperlipoproteinaemia and hyperlipidemia are provided, as are novel methods for preparation and intermediate compounds.

13 Claims, No Drawings

SULFUR-CONTAINING HMG-COA REDUCTASE INHIBITORS

FIELD OF THE INVENTION

The present invention relates to new sulfur-containing compounds which inhibit the activity of 3-hydroxy-3-methylglutaryl-coenzyme A (HMG-CoA) reductase and thus are useful in inhibiting cholesterol biosynthesis, to pharmaceutical compositions containing such compounds, to methods for preparing, and new intermediates formed in the preparation of such compounds, and to methods of using such compounds.

SUMMARY OF THE INVENTION

The instant invention provides compounds having a sulfur-containing group, which group preferably binds to the HMG binding domain of HMG-CoA reductase, linked by an acetylenic or ethylenic linkage to a hydrophobic group, which group is preferably a lipophilic anchor group capable of binding to a hydrophobic part of HMG-CoA reductase not utilized in binding HMG-CoA. The compounds of the instant invention are inhibitors of the enzyme 3-hydroxy-3-methylglutaryl coenzyme A reductase (HMG-CoA reductase) and are thus inhibitors of cholesterol biosynthesis (hypocholesterolemic agents). The instant invention therefore provides a method and pharmaceutical compositions for reducing or maintaining plasma cholesterol levels. The instant invention also provides methods and pharmaceutical compositions for the treatment and/or prevention of atheroschlerosis, hyperlipodemia, and hyperlipoproteinaemia.

The inventive compounds are advantageous in that they are readily synthesized by the novel methods also provided by the instant invention. Further provided are the novel intermediates produced in the preparation of the inventive compounds.

DETAILED DESCRIPTION OF THE INVENTION

Compounds are provided having the following formulae I or II:

$$(O)_n = S - CH_2 - \underset{\underset{\underset{\underset{Z}{|}}{\overset{|||}{C}}}{\overset{|}{C}}}{\overset{OH}{\underset{|}{C}}} - CH_2 - \overset{O}{\overset{||}{C}} - OR^1 \quad (I)$$

$$(O)_n = S - CH_2 - \underset{\underset{\underset{Z}{|}}{\overset{||}{C}}}{\overset{|}{C}} - CH_2 - \overset{O}{\overset{||}{C}} - OR^1 \quad (II)$$
(cis or trans)

where
n is zero, 1 or 2;
R is hydrogen or lower alkyl;
Z is a hydrophobic group, preferably a lipophilic anchor group which is capable of binding to a hydrophobic part of HMG-CoA reductase not utilized in binding HMG-CoA; and
$R^1$ is (i) hydrogen,
(ii) alkyl,
(iii) aryl,
(iv) the group $$-\underset{R^2}{\overset{|}{C}}H - O - \overset{O}{\overset{||}{C}} - R^3,$$

where $R^2$
is hydrogen, alkyl or aryl and $R^3$ is alkyl or aryl, or (v) if not already covered above, a group forming, together with the atoms to which it is bonded, an ester group which is hydrolyzable in vivo;

and salts, preferably pharmaceutically acceptable salts, thereof. Reference to a compound or salt herein is defined to include solvates such as hydrates thereof, unless otherwise indicated.

The group $$(O)_n = S - CH_2 - C(R)(OH) - CH_2 - C(O)OR^1$$

of the compounds of formulae I and II preferably is capable of binding to the HMG binding domain of HMG-CoA reductase. The capability of binding to the HMG binding domain of HMG-CoA reductase may be indicated, for example, by the ability of a compound to inhibit the activity of that enzyme. With respect to the group Z, the capability of binding to a hydrophobic part of HMG-CoA reductase not utilized in binding HMG-CoA may be indicated, for example, by an enhanced potency of the compound containing that group in inhibiting the activity of HMG-CoA reductase relative to the activity exhibited by the corresponding compound in which Z is hydrogen.

The group R is preferably hydrogen.

The group $R^1$ is preferably hydrogen or a salt cation, especially an alkali metal cation. When $R^1$ is the group $$-\underset{R^2}{\overset{|}{C}}H - O - \overset{O}{\overset{||}{C}} - R^3, R^2$$

is preferably hydrogen or lower alkyl and $R^3$ is preferably lower alkyl.

Compounds of the formula I or salts thereof are preferred. With respect to formula II, such as where R is hydrogen, compounds or salts thereof where Z is, for example, not phenylmethylene, naphthylmethylene or a moiety bonded to the group —CH=CH— (cis or trans) through a phenylmethylene or naphthylmethylene group may be prepared.

The hydrophobic anchor group Z is preferably an aryl, cycloalkyl, 2,2-diarylalkenyl or heterocyclo group. Exemplary Z groups include the following groups (i) to (xxiii):

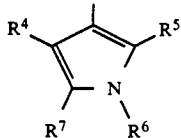

(i)

where one of R⁴ and R⁵ is substituted phenyl and the other of R⁴ and R⁵ is lower alkyl; R⁷ and R⁶ together are —(CH=CH)₂— or —(CH₂)₄— and are joined to complete a six membered carbocyclic ring;

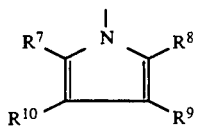

(ii)

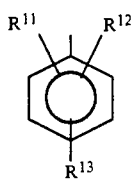

(iii)

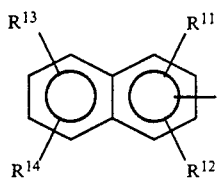

(iv)

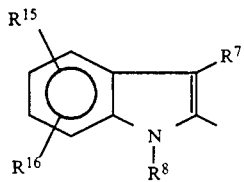

(v)

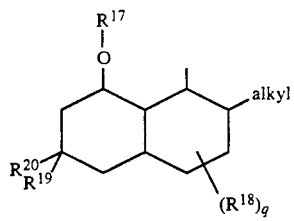

(vi)

an exemplary group (vi) being the following group (vi)(a):

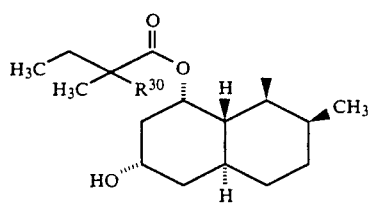

(vi)(a)

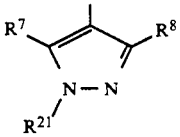

(vii)

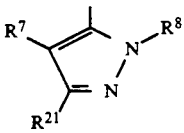

(viii)

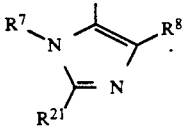

(ix)

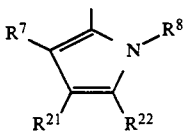

(x)

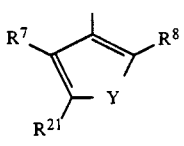

(xi)

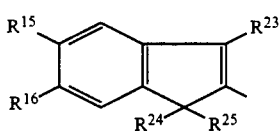

(xii)

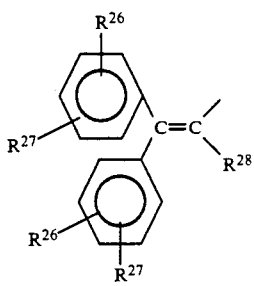

(xiii)

wherein R¹¹, R¹², R¹³ and R¹⁴ are the same or different and are each independently selected from hydrogen, halogen, lower alkyl (such as lower haloalkyl), phenyl, substituted phenyl or OR²⁹ (wherein R²⁹ is hydrogen, alkanoyl, benzoyl, phenyl, substituted phenyl such as halophenyl, phenyl-lower alkyl, alkyl such as haloalkyl, cinnamyl, allyl, cycloalkyl-lower alkyl, adamantyl-lower alkyl or substituted phenyl-lower alkyl), and where a dotted line denotes an optional double bond;

where Z is (vi), R¹⁹ and R²⁰ are the same or different and are hydrogen, lower alkyl or OH; R¹⁷ is lower

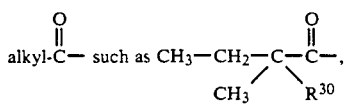

or aryl(CH$_2$)—; R$^{18}$ is lower alkyl, hydroxy, oxo or halogen, q is 0, 1, 2 or 3; and R$^{30}$ is hydrogen, alkyl, cycloalkyl, aryl or aralkyl;

where Z is (ii), (v), (vii), (viii), (ix), (x), or (xi), one of R$^7$ and

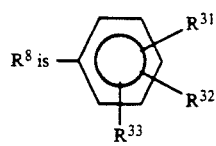

R$^8$ is and the other is lower alkyl, cycloalkyl or phenyl—(CH$_2$)$_p$—; p is 0, 1, 2, 3 or 4; R$^{31}$ is hydrogen, lower alkyl, lower alkoxy (preferably other than t-butoxy), halogen, phenoxy or benzyloxy; R$^{32}$ is hydrogen, lower alkyl, lower alkoxy, halogen, phenoxy or benzyloxy; R$^{33}$ is hydrogen, lower alkyl, lower alkoxy, or halogen (and, preferably, with the provisos that both R$^{32}$ and R$^{33}$ are hydrogen when R$^{31}$ is hydrogen, R$^{33}$ is hydrogen when R$^{32}$ is hydrogen, not more than one of R$^{31}$ and R$^{32}$ is trifluoromethyl, not more than one of R$^{31}$ and R$^{32}$ is phenoxy and not more than one of R$^{31}$ and R$^{32}$ is benzyloxy); R$^{15}$ is hydrogen, C$_{1-4}$ alkyl, C$_{3-6}$ cycloalkyl, C$_{1-4}$ alkoxy (preferably other than t-butoxy), trifluoromethyl, fluoro, chloro, phenoxy or benzyloxy, R$^{16}$ is hydrogen, C$_{1-3}$ alkyl, C$_{1-3}$ alkoxy, trifluoromethyl, fluoro, chloro, phenoxy or benzyloxy (and, preferably, with the provisos that R$^{16}$ is hydrogen when R$^{15}$ is hydrogen, not more than one of R$^{15}$ and R$^{16}$ is trifluoromethyl, not more than one of R$^{15}$ and R$^{16}$ is phenoxy, and not more than one of R$^{15}$ and R$^{16}$ is benzyloxy); R$^{21}$ and R$^{22}$ are independently selected from hydrogen, alkyl, cycloalkyl, adamantyl-1 or

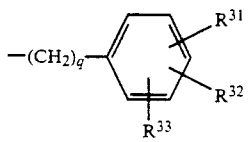

where R$^{31}$, and R$^{33}$ are as defined above and q is 0, 1, 2, 3 or 4; and Y is O, S or N—R$^{21}$;

where Z is (xii), R$^{24}$ is hydrogen or primary or secondary C$_{1-6}$ alkyl; R$^{25}$ is primary or secondary C$_{1-6}$ alkyl; or R$^{24}$+R$^{25}$ is (CH$_2$)$_r$ or (cis)CH$_2$—CH═CH—CH$_2$; r=2, 3, 4, 5 or 6; R is lower alkyl, cycloalkyl or

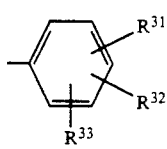

wherein R$^{15}$, R$^{16}$, R$^{31}$, R$^{32}$ and R$^{33}$ are as defined above;

where Z is (ii), R$^{10}$ and R$^9$ are both H, Cl, Br, CN, CF$_3$, phenyl, 1-4C alkyl, 2-8C alkoxycarbonyl, —CH$_2$OR$^{34}$ or —CH$_2$OCONHR$^{35}$, R$^{34}$ is H or 1-6C alkanoyl; R$^{35}$ is alkyl or phenyl optionally substituted by F, Cl, Br or 1-4C alkyl; or R$^{10}$ and R$^9$ taken together are —(CH$_2$)$_s$—, —CH$_2$OCH$_2$—, —CON(R$^{36}$)CO—, or —CON(R$^{37}$)N(R$^{38}$)CO—; s=3 or 4; R$^{36}$=H, 1-6C alkyl, phenyl or benzyl; R$^{37}$ and R$^{38}$ are H, 1-4C alkyl or benzyl;

where Z is (xiii), R$^{28}$ is lower alkyl, cycloalkyl, adamantyl-1 or

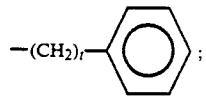

t=1, 2, 3 or 4; R$^{26}$ and R$^{27}$ are the same or different and are each independently selected from hydrogen, lower alkyl, lower alkoxyl (preferably other than t-butoxy), halogen, phenoxy or benzyloxy (and, preferably, with the provisos that R$^{27}$ must be hydrogen when R$^{26}$ is hydrogen, not more than one of R$^{26}$ and R$^{27}$ is trifluoromethyl, not more than one of R$^{26}$ and R$^{27}$ is phenoxy, and not more than one of R$^{26}$ and R$^{27}$ is benzyloxy);

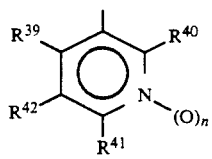

(xiv)

where
R$^{39}$ and R$^{40}$ are the same or different and are each independently selected from
(i) hydrogen,
(ii) alkyl,
(iii) aryl,
(iv) cycloalkyl,
(v) aralkyl,
(vi) aralkoxy,
(vii) alkenyl,
(viii) cycloalkenyl, and
(ix) heterocyclo;
R$^{41}$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) halo-substituted alkyl,
(xi) adamantyl, and
(xii) heterocyclo;
R$^{42}$ is selected from
(i) hydrogen,
(ii) lower alkyl,
(iii) aryl,
(iv) cycloalkyl,
(v) alkoxy,
(vi) aralkyl,
(vii) aralkoxy,
(viii) alkenyl,
(ix) cycloalkenyl,
(x) adamantyl,
(xi) halogen,
(xii) halo-substituted alkyl, and
(xiii) heterocyclo;
or R$^{41}$ and R$^{42}$ taken together can be

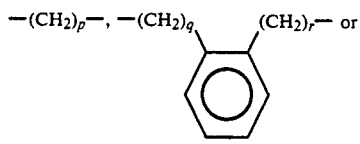

—(CH=CH)$_2$—;
n is 0 or 1;
p is 3, 4 or 5;
q is 0, 1, 2, or 3; and
r is 0, 1, 2, or 3;

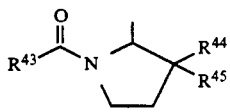 (xv)

R$^{43}$ is aryl or alkyl;
R$^{44}$ and R$^{45}$ are the same or different and are hydrogen, lower alkyl or aryl; or R$^{44}$ and R$^{45}$ taken together form a cycloalkyl group;

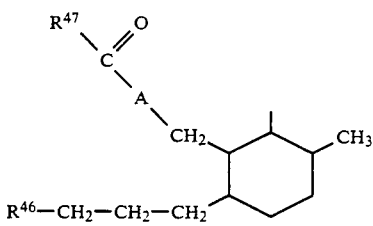 (xvi)

R$^{46}$ is hydrogen, lower alkyl, aryl, lower alkoxy, cycloalkyl, heterocyclo, aralkyl, or heterocycloalkyl;
R$^{47}$ is lower alkyl, cycloalkyl or aralkyl;
A is O or NR$^{48}$, wherein R$^{48}$ is hydrogen or lower alkyl;

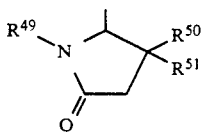 (xvii)

R$^{49}$ is hydrogen, alkyl, alkenyl, aryl, alkylaryl,
one of R$^{50}$ and R$^{51}$ is hydrogen, and the other is hydrogen, alkyl, alkenyl, aryl, or alkylaryl; or and R$^{50}$ and R$^{51}$ are both lower alkyl; or
R$^{50}$ and R$^{51}$ together complete a hydrocarbon ring that is cycloalkyl or cycloalkenyl;
a 5-pyrazolopyridinyl group, or a moiety containing, and bonded through, a 5-pyrazolopyridinyl group such as:

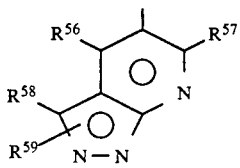 (xviii)

where R$^{56}$, R$^{57}$, R$^{58}$ and R$^{59}$ are independently
(i) hydrogen
(ii) alkyl,
(iii) aryl,
(iv) aralkyl,
(v) aralkoxy,
(vi) heterocyclo,
(vii) cycloalkyl,
(viii) alkoxy,
(ix) alkenyl,
(x) cycloalkenyl,
(xi) halogen,
(xii) hydroxy,
(xiii) amino,
(xiv) alkylamino, or
(xv) dialkylamino;
a 5-pyrimidinyl group, or a moiety containing, and bonded through, a 5-pyrimidinyl group such as:

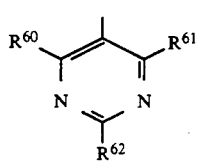 (xix)

where R$^{60}$, R$^{61}$ and R$^{62}$ are independently
(i) hydrogen,
(ii) alkyl,
(iii) aryl,
(iv) aralkyl,
(v) aralkoxy,
(vi) heterocyclo,
(vii) cycloalkyl,
(viii) alkoxy,
(ix) alkenyl,
(x) cycloalkenyl, or
(xi) halogen;

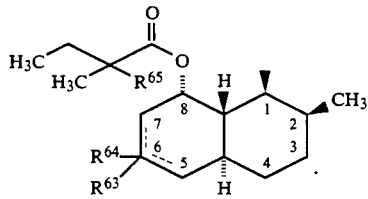 (xx)

where
R$^{63}$ and R$^{64}$ are each independently fluoro or hydrogen, except that at least one of R$^{63}$ and R$^{64}$ is fluoro;
R$^{65}$ is hydrogen, alkyl, cycloalkyl, aryl, or arylalkyl;
and wherein carbons 5 to 6 are single- or double-bonded and carbons 6 to 7 are single- or double-bonded, except that carbons 5 to 6 and 6 to 7 are not both double-bonded;

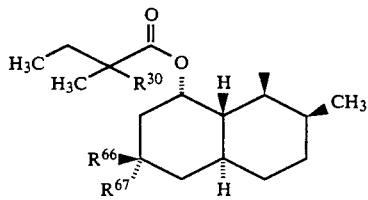 (xxi)

where
R$^{66}$ is hydrogen or —S(O)$_m$—R$^{68}$ and R$^{67}$ is hydrogen or S(O)$_n$—R$^{69}$, except that R$^{66}$ and R$^{67}$ are not both hydrogen, or one of $R^{66}$ and $R^{67}$ is —S-alkylene-SH and the other is hydrogen;

$R^{68}$ and $R^{69}$ are each independently hydrogen, acyl, alkyl, alkenyl, alkynyl, aryl, aralkyl,

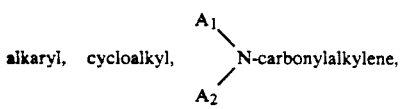

alkoxycarbonylalkylene or trifluoromethyl or $R^{68}$ and $R^{69}$ together are alkylene of 1 to 6 carbon atoms;

$A_1$ and $A_2$ are each independently hydrogen, alkyl, or alkaryl;

m is 0, 1, or 2; and n is 0, 1 or 2;

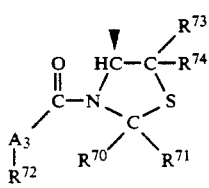 (xxii)

where $R^{70}$ and $R^{71}$ are the same or different and are hydrogen, lower alkyl or aryl;

$A_3$ is

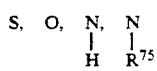

or a single bond, $R^{75}$ is lower alkyl; $R^{72}$ is lower alkyl or aryl; $R^{73}$ and $R^{74}$ are the same or different and are hydrogen or lower alkyl; and, particularly,

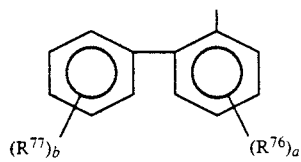 (xxiii)

where a is 1, 2, 3 or 4 and each $R^{76}$ substituent is independently selected from (i) hydrogen,
(ii) alkyl,
(iii) aryl,
(iv) aralkyl,
(v) aralkoxy,
(vi) heterocyclo,
(vii) cycloalkyl,
(viii) alkoxy,
(ix) alkenyl,
(x) cycloalkenyl,
(xi) halogen,
(xii) hydroxy,
(xiii) amino,
(xiv) alkylamino, or
(xv) dialkylamino; and b is 1, 2, 3, 4 or 5 and each $R^{77}$ substituent is independently selected from those groups (i) to (xv) described above for $R^{76}$.

The above exemplary groups Z are described, for example, in (a) U.S. Pat. No. 5,724,453, issued Jun. 23, 1992 to Karanewsky (group (i)); (b) U.S. Pat. No. 5,091,378, issued Feb. 25, 1992 to Karanewsky et al. Ser. No. 07/182,710, filed Apr. 18, 1988 (groups (ii) to (xiii)); (c) U.S. application Ser. No. 07/588,800, filed Sep. 27, 1990 to Robl (group (xiv)); (d) U.S. Pat. No. 5,049,578, issued Sep. 17, 1991 to Varma et al. (group (xv)); (e) U.S. Pat. No. 5,189,180, issued Feb. 23, 1993 to Karanewsky filed May 1, 1991 (group (xvi)); (f) U.S. Pat. No. 5,197,104, issued Jan. 5, 1993 to Varma et al. (group (vi)(a)); (g) U.S. Pat. No. 5,049,577, issued Sep. 17, 1991 to Varma et al. (group (xvii)); (h) U.S. application Ser. No. 07/754,886, filed Sep. 4, 1991 to Robl (group (xviii)); (i) U.S. Pat. No. 5,202,327, issued Apr. 13, 1993 to Robl (group (xix)); (j) U.S. Pat. No. 5,089,523, issued Feb. 18, 1992 to Varma et al. Ser. No. 521,880, filed May 11, 1990 (group (xx)); (k) U.S. application Ser. No. 07/724,272, filed Jul. 1, 1991 to Varma et al. (group (xxi)); and (l) U.S. Pat. No. 5,106,992, issued Apr. 21, 1992 to Magnin et al.; all of the above documents ((a) through (l)) incorporated herein by reference.

The term "alkyl" as employed herein alone or as part of another group preferably denotes both straight and branched chain hydrocarbons containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including one or more halo-substituents, (e.g. F, Br, Cl or I, or $CF_3$), for example, trihalomethyl, alkoxy substituents, aryl substituents, alkyl-aryl substituents, haloaryl substituents, cycloalkyl substituents, alkyl-cycloalkyl substituents, hydroxy substituents, alkylamino substituents, alkanoylamino substituents, arylcarbonylamino substituents, nitro substituents, cyano substituents, thiol substituents or alkylthio substituents. The term "lower alkyl" as employed herein preferably denotes such alkyl groups as described above containing 1 to 6 carbon atoms in the normal chain.

The term "alkenyl" as employed herein alone or as part of another group preferably denotes such groups as described above for alkyl, further containing at least one carbon to carbon double bond.

The term "alkynyl" as employed herein alone or as part of another group preferably denotes such groups described above for alkyl, further containing at least one carbon to carbon triple bond.

The term "cycloalkyl" as employed herein alone or as part of another group preferably denotes saturated cyclic hydrocarbon groups containing one to three rings and 3 to 12 ring carbons, preferably 3 to 8 ring carbons, which include cyclopropyl, cyclobutyl, cyclopentyl, cyclohexyl, cycloheptyl, cyclooctyl, cyclodecyl, cyclododecyl, and adamantyl, any of which groups may be substituted, for example, with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "cycloalkenyl" as employed herein alone or as part of another group preferably denotes such groups as described above for cycloalkyl, further containing at least one carbon to carbon double bond in the ring system.

The term "acyl" as employed herein refers to all organic moieties which may be derived from an organic carboxylic acid by removal of the hydroxyl group.

The term "aryl" as employed herein preferably denotes monocyclic or bicyclic substituted or unsubstituted aromatic groups containing from 6 to 12 carbons in the ring portion, such as phenyl, biphenyl, naphthyl, substituted phenyl, substituted biphenyl or substituted naphthyl wherein the substituent may be 1, 2 or 3 alkyl, preferably lower alkyl, groups, halogen(s) (e.g., Cl, Br or F), 1, 2 or 3 alkoxy, preferably lower alkoxy, groups, 1, 2 or 3 hydroxy groups, 1, 2 or 3 phenyl groups, 1, 2 or 3 phenoxy groups, 1, 2 or 3 alkanoyloxy groups, 1, 2 or 3 benzoyloxy groups, 1, 2 or 3 haloalkyl groups, 1, 2 or 3 haloalkoxy groups, 1, 2 or 3 halophenyl groups, 1, 2 or 3 allyl groups, 1, 2 or 3 cycloalkyl groups, 1, 2 or 3 cycloalkylalkyl groups, 1, 2 or 3 alkylamino groups, 1, 2 or 3 dialkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, 1, 2 or 3 thiol groups, 1, 2 or 3 (alkyl)$_3$silyloxy or (phenyl)$_2$(alkyl)silyloxy groups, methylenedioxy where the methylene group may be substituted by 1 or 2 lower alkyl groups, 1, 2 or 3 arylalkenyl groups, and/or 1, 2 or 3 alkylthio groups.

The terms "aralkyl", "aryl-alkyl" or "aryl-lower alkyl" as used herein alone or as part of another group refer to alkyl or lower alkyl groups as discussed above having an aryl substituent, such as benzyl.

The terms "lower alkoxy", "alkoxy", or "aryloxy" or "aralkoxy" as employed herein alone or as part of another group include any of the above lower alkyl, alkyl, aryl or aralkyl groups linked to an oxygen atom.

The terms "lower alkylthio", "alkylthio", "arylthio", or "aralkylthio" as employed herein alone or as part of another group include any of the above lower alkyl, alkyl, aryl or aralkyl groups linked to a sulfur atom.

The terms "lower alkylamino", "alkylamino", "arylamino", or "arylalkylamino" as employed herein alone or as part of another group include any of the above lower alkyl, alkyl, aryl or arylalkyl groups linked to a nitrogen atom.

The term "alkanoyl" as used herein alone or as part of another group refers to an alkyl group linked to a carbonyl group.

The term "halogen" or "halo" as used herein refers to chlorine, bromine, fluorine, and iodine, with chlorine or fluorine being preferred.

The term "heterocyclo" preferably denotes fully saturated or unsaturated, monocyclic or bicyclic, aromatic or nonaromatic hydrocarbon groups having 5 or 6 atoms in each ring and at least one heteroatom in at least one ring. The heterocyclo group has 1 or 2 oxygen atoms, 1 or 2 sulfur atoms, and/or 1 to 4 nitrogen atoms in the ring. The heterocyclo group may be substituted with halogen(s), 1, 2 or 3 lower alkoxy groups, 1, 2, or 3 aralkyl groups, 1, 2 or 3 hydroxy groups, 1, 2 or 3 phenyl groups, 1, 2 or 3 alkanoyloxy groups, 1, 2 or 3 benzoyloxy groups, 1, 2 or 3 halophenyl groups, 1, 2 or 3 alkyl groups, 1, 2 or 3 alkylamino groups, 1, 2 or 3 alkanoylamino groups, 1, 2 or 3 arylcarbonylamino groups, 1, 2 or 3 amino groups, 1, 2 or 3 nitro groups, 1, 2 or 3 cyano groups, and 1, 2 or 3 thiol groups. Exemplary heterocyclo groups are 2- and 3-thienyl, 2- and 3-furyl, 2- and 3-pyrrolyl, 2-, 3- and 4-pyridyl, 2-, 4- and 5-imidazolyl, 2- and 3-pyrrolidinyl, 2-, 3- and 4-piperidinyl, 2-, 3- and 4-azepinyl, 4-, 5-, 6- or 7-indolyl, 4-, 5-, 6- or 7-isoindolyl, 5-, 6-, 7- or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6- or 7-benzoxadiazolyl, and 4-, 5-, 6- or 7-benzofurazanyl.

The term "salt(s)" refers to acidic and/or basic salts formed with inorganic and organic acids and bases. Basic salts are preferred. Exemplary basic salts include ammonium salts such as alkylammonium salts, alkali metal salts such as lithium, sodium and potassium salts (which are preferred), alkaline earth metal salts such as calcium and magnesium salts, salts with organic bases, for example, amine salts such as dicyclohexylamine salt, benzathine, N-methyl-D-glucamine, hydrabamine salts, salts with amino acids such as arginine and lysine and equivalent such salts. The nontoxic, pharmaceutically acceptable salts are preferred, although other salts are also useful, for example, in isolation or purification steps which may be employed during preparation.

All stereoisomers of the compounds of the instant invention are contemplated, either in admixture or in pure or substantially pure form. Compounds of the formulae I or II or salts thereof where n is 1 may be prepared as one or both of the two diastereoisomers which may be formed (based on the position of the groups attached to the sulfinyl group). For all compounds of the formulae I or II or salts thereof (that is, where n is 0, 1 or 2), the chiral center

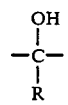

of the sulfur-containing side chain is preferably of the same absolute configuration corresponding to that where R=hydrogen and the group —OH is of the S configuration.

The compounds of the instant invention may, for example, be in the free or solvate, such as hydrate form, and may be obtained by the following novel methods of the invention.

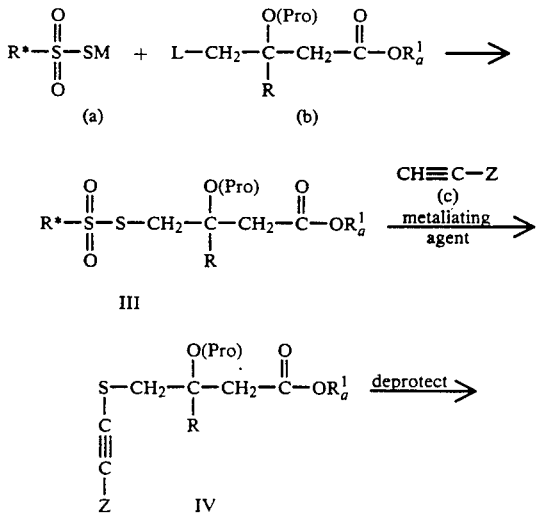

-continued
Reaction Scheme I
Method for the Preparation of
Compounds of the Formula I, n = 0

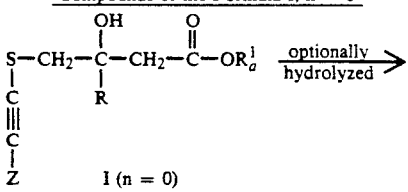

I (n = 0)

$$\xrightarrow{\text{optionally hydrolyzed}}$$

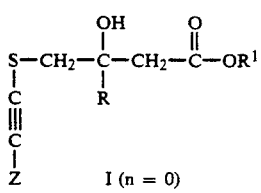

I (n = 0)

Compounds of the formula I where n is zero may be prepared as shown above in Reaction Scheme I.

Reaction Scheme I begins by reacting a compound (a) with a compound (b) to produce a compound of the formula III, where $R_a^1$ is $R^1$ as defined for the formula I except that $R_a^1$ may not be hydrogen, Pro is a protecting group which may be cleaved in subsequent steps without the destruction of the remainder of the molecule, and is preferably —Si(t-butyl)(diphenyl), L is a leaving group such as mesylate, tosylate, triflate or, especially, a halogen, most preferably iodo, R* is heterocyclo such as heteroaromatic, or alkyl, alkenyl, cycloalkyl, cycloalkenyl, or, preferably, aryl such as benzyl, particularly p-methylbenzyl, and M is an alkali metal such as potassium.

Compounds of the formula (a) are known and may be prepared by the skilled artisan. Compounds of the formula (b) may also be prepared by the skilled artisan as discussed following. For example, a compound of the formula (b) having the preferred iodo leaving group L may be prepared starting with the following bromide:

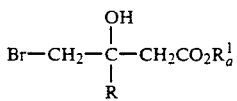

where the above bromide may itself be prepared by employing procedures analogous to those described in Acta. Chem. Scand., B., 1983, 37, 341-344.

The bromide may be dissolved in solution in dimethylformamide (DMF) with imidazole and 4-dimethylamino pyridine, and the resulting solution treated with the halide of the protecting group "Pro", e.g. with t-butyldiphenyl silyl chloride, under an inert atmosphere such as argon to form the following protected ether:

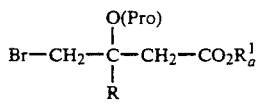

A solution of the above protected ether in an inert organic solvent such as methyl ethyl ketone or DMF may be treated with sodium iodide under an inert atmosphere such as argon, to form iodide compound (b).

The reaction of compounds (a) and (b) is preferably conducted at a temperature of from about 0° C. to about 100° C., most preferably from about 50° C. to about 75° C.; and preferably at a pressure of from about 1 atm to about 5 atm. The reaction is preferably completed over the course of about 1 hour to about 24 hours, and is preferably conducted under an atmosphere of nitrogen or argon.

Molar ratios of compound (a) to compound (b) are preferably from about 1:1 to about 10:1, particularly from about 1:1 to about 3:1. Solvents are preferably employed which are selected from organic or inorganic solvents such as acetonitrile or dimethylsulfoxide (DMSO), most preferably dimethylformamide. Amounts of solvents are preferably those where the compound (b) starting material is from about 1 to about 5% by weight, based on the combined weight of solvent and compound (b).

The above reaction method, and the compounds of the formula III produced, are novel.

The compound of formula III is then contacted with a compound (c) and a metallating agent, yielding the compound of formula IV. Preferably, the compound (c) is pre-contacted with the metallating agent to form a metallated anion of the compound (c) prior to contact with the formula III compound. Preferred metallating agents are organic lithium compounds such as t-butyl and n-butyl lithium.

Compounds of the formula (c) may be obtained according to methods such as those described in the patents and patent applications (a) through (1) recited above and incorporated herein by reference.

The reaction involving the compound of formula III and the compound (c) is preferably conducted at a temperature of from about $-100°$ C. to about 40° C., most preferably from about $-78°$ C. to about 0° C.; and preferably at a pressure of from about 1 atm to about 5 atm. The reaction is preferably completed over the course of about 1 hour to about 24 hours, and is preferably conducted under an atmosphere of inert gas such as argon.

Molar ratios of compound (c) to the compound of formula III are preferably from about 1:1 to about 1:5, particularly from about 1:1 to about 1:2. Solvents are preferably employed which are selected from dry organic solvents such as acetonitrile or dimethylformamide (DMF), most preferably tetrahydrofuran. Amounts of solvents are preferably those where the formula III starting material is from about 1 to about 5% by weight, based on the combined weight of solvent and formula III compound.

The same conditions, for example, temperature, solvent employed and the like, as described above for contacting the compound (c) with the compound of formula III are preferably employed for precontacting the formula (c) compound and metallating agent to form the metallated anion of the formula (c) compound. Molar ratios of metallating agent to compound (c) are preferably those from about 1:1 to about 1:3, particularly those from about 1:1 to about 1:1.5.

The above reaction method and compounds of the formula IV are novel.

The group "Pro" of the compound of the formula IV may then be cleaved to form a compound of the formula I. For example, when —O—(Pro) is a silyl ether, cleavage may be effected by treating the formula IV compound with a cleaving agent such as acetic acid and tetrabutylammonium fluoride, or with HCl or other inorganic acids.

The cleavage is preferably conducted at a temperature of from about −50° C. to about +50° C., most preferably from about 0° C. to about 30° C.; and preferably at a pressure of from about 1 atm to about 5 atm. Cleavage is preferably completed over the course of about 1 hour to about 24 hours, and is preferably conducted under an atmosphere of nitrogen or argon.

Molar ratios of cleaving agent to the compound of the formula IV are preferably from about 1:1 to about 1:10, particularly from about 1:2 to about 1:5. Solvents are preferably employed which are selected from dry organic solvents such as acetonitrile or dimethylformamide, most preferably tetrahydrofuran. Amounts of solvents are preferably those where the formula IV starting material is from about 1 to about 5% by weight, based on the combined weight of solvent and formula IV compound.

The cleavage method, producing the inventive compounds of the formula I where n is zero, is novel.

Compounds of the formula I having the ester group $R_a^1$ may optionally be hydrolyzed. Hydrolysis may be conducted, for example, by treatment with a strong base such as lithium hydroxide or sodium hydroxide in the presence of dioxane, methanol, acetonitrile, tetrahydrofuran or other inert organic solvent under an inert atmosphere such as argon, preferably at a temperature of from about room temperature to about 80° C. A molar ratio of base:ester of from about 1:1 to about 1.1:1 is preferred. The basic salt formed may then be treated with a strong acid such as HCl to form the corresponding acid.

Hydrolysis, producing the inventive compounds of the formula I, is novel.

Reaction Scheme II
Method for the Preparation of
Compounds of the Formula I, n = 1

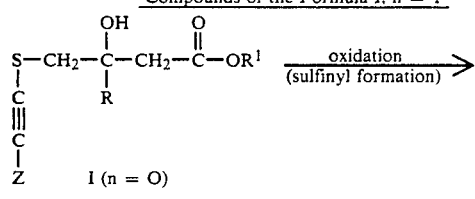

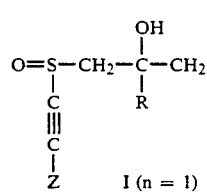

Compounds of the formula I where n is zero, prepared as in Reaction Scheme I above, may be employed in Reaction Scheme II for the preparation of compounds of the formula I where n is 1.

According to Reaction Scheme II, a compound of the formula I having the thio group —S— is contacted with an oxidizing agent capable of transforming the thio group to a sulfinyl group

Exemplary oxidizing agents capable of such transformation include m-chloroperbenzoic acid, peracetic acid in a chlorinated hydrocarbon solvent such as methylene chloride, chloroform, 1,2-dichloroethane or the like, (n-butyl)$_4$N$^+$IO$_4^-$ in refluxing chloroform or hydrogen peroxide, particularly an alkali metal metaperiodate such as sodium metaperiodate.

The oxidation is preferably conducted at a temperature of from about 0° C. to about 50° C.; most preferably from about 20° C. to about 30° C.; and preferably at a pressure of from about 1 atm to about 5 atm. The reaction is preferably completed over the course of about 1 hour to about 24 hours, and is preferably conducted under an atmosphere of inert gas such as argon.

Molar ratios of oxidizing agent to the starting compound of the formula I (n=0) are preferably about 1:1. Solvents are preferably employed which are selected from organic or inorganic solvents such as methylene chloride or acetic acid, most preferably a mixture of methanol and water. Amounts of the solvent are preferably those where the formula I starting material is from about 1 to about 5% by weight, based on the combined weight of solvent and formula I compound.

The oxidizing method is novel.

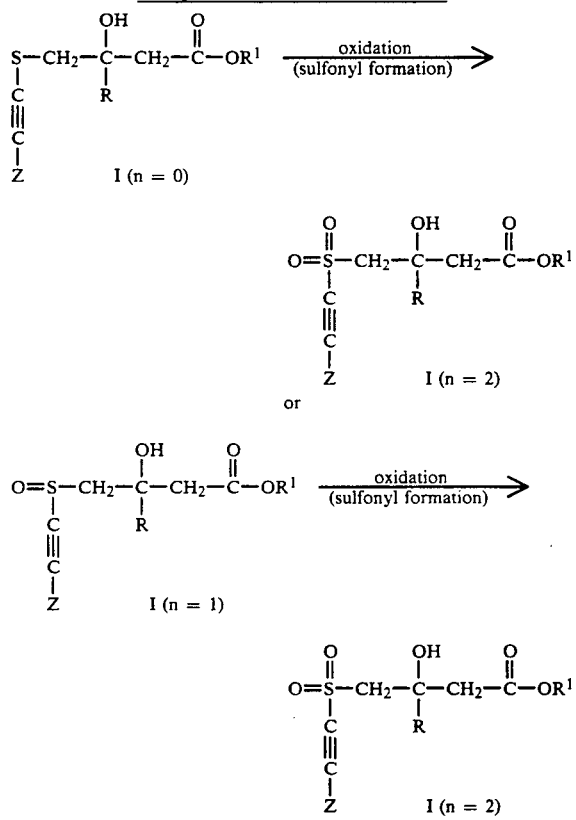

Compounds of the formula I where n is zero prepared as in Reaction Scheme I above, or compounds of the formula I where n is 1 prepared as in Reaction Scheme II above, may be employed in Reaction Scheme III for the preparation of compounds of the formula I where n is 2.

According to Reaction Scheme III, a compound of the formula I having the thio group —S— or the sulfinyl group

is contacted with an oxidizing agent capable of transforming the thio or sulfinyl group to a sulfonyl group

Exemplary oxidizing agents capable of such transformation include those recited for Reaction Scheme II. m-Chloroperoxybenzoic acid is preferred as the oxidizing agent.

The oxidation is preferably conducted at a temperature of from about −50° C. to about 50° C.; most preferably from about 20° C. to about 30° C.; and preferably at a pressure of from about 1 atm to about 5 atm. The reaction is preferably completed over the course of about 1 hour to about 24 hours, and is preferably conducted under an atmosphere of nitrogen.

Molar ratios of oxidizing agent to the compound of formula I where n=zero are preferably from about 2:1 to about 10:1, particularly from about 4:1 to about 6:1. Molar ratios of oxidizing agent to the compound of formula I where n=1 are preferably from about 1:1 to about 10:1, particularly from about 4:1 to about 6:1. Solvents are preferably employed which are selected from organic solvents such as methylene chloride, most preferably trichloromethane. Amounts of solvents are preferably those where the formula I starting material is from about 1 to about 5% by weight, based on the combined weight of solvent and formula I compound.

The oxidation method is novel.

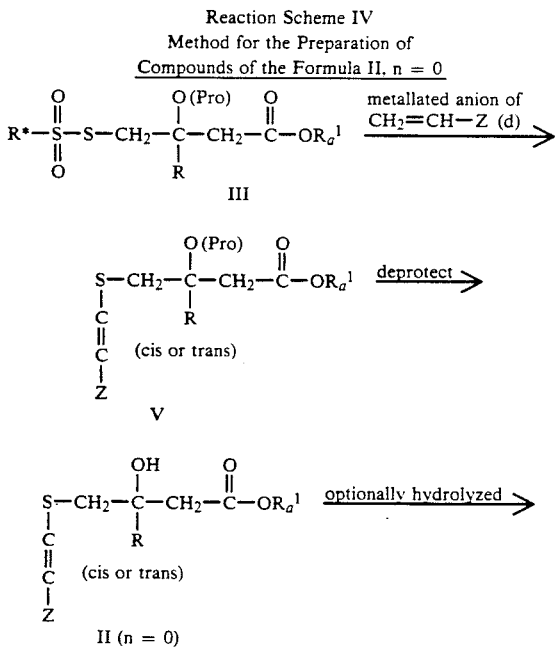

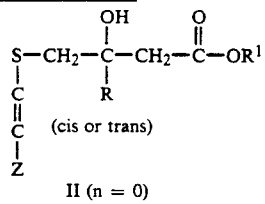

Compounds of the formula II where n is zero may be prepared as shown in Reaction Scheme IV. Reaction Scheme IV begins by reacting a compound of the formula III, prepared as in Reaction Scheme I above, with a compound (d), that is, the metallated anion of the compound Z—CH=CH$_2$, to produce a compound of the formula V. The compound of formula (d) may be prepared by the following procedure, beginning with the aldehyde:

Z—CHO.

The above aldehyde may be obtained according to methods such as those described in the patents and patent applications (a) through (1) recited above and incorporated herein by reference. Reaction of the aldehyde with tetrabromomethane in the presence of triphenylphosphine and a dry, inert organic solvent such as dichloromethane at low (for example, −10° C.) temperatures produces the dibromovinyl compound —CH=C(Br)$_2$.

The above dibromovinyl compound may be dehalogenated by contact with tin hydride (SnH$_4$) to produce the bromovinyl compound Z—CH=CHBr.

The above bromovinyl compound may then be converted directly to the compound (d) by contact with a metallating agent, thereby forming the metallated anion of the compound Z—CH=CH$_2$. Preferred metallating agents are organic lithium compounds such as t-butyl and n-butyl lithium.

The reaction involving the compound of formula III and the compound (d) is preferably conducted at a temperature of from about −100° C. to about 50° C., most preferably from about −78° C. to about 0° C.; and preferably at a pressure of from about 1 atm to about 5 atm. The reaction is preferably completed over the course of about 1 hour to about 24 hours, and is preferably conducted under an atmosphere of nitrogen or argon.

Molar ratios of compound (d) to the compound of formula III are preferably from about 1:1 to about 1:3, particularly from about 1:1 to about 1:2. Solvents are preferably employed which are selected from inorganic and organic solvents such as tetrahydrofuran or ethyl ether. Amounts of solvents are preferably those where the formula III starting material is from about 1 to about 5% by weight, based on the combined weight of solvent and formula III compound.

Compounds of the formula V, prepared as above, contain both the cis and trans stereoisomeric forms. These stereoisomers may be separated, or may be retained as a mixture in the subsequent procedures of Reaction Scheme IV. Deprotection, and optional hydrolysis, of compounds of the formula V to produce compounds of the formula II may be achieved by the methods described above for the compounds of the formula I.

Compounds of the formula V are novel, as is the method described herein for preparation of these compounds. Also novel are the methods to deprotect and, optionally, hydrolyze compounds of the formula V to prepare the compounds of the formula II.

Reaction Scheme V
Method for the Preparation of
Compounds of the Formula II, n = 1

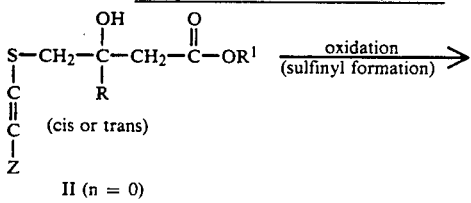

II (n = 0)

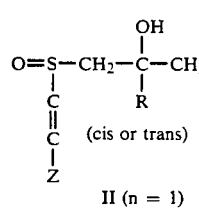

II (n = 1)

Compounds of the formula II where n is zero, prepared as in Reaction Scheme IV above, may be employed in Reaction Scheme V for the preparation of compounds of the formula II where n is 1.

According to Reaction Scheme V, a compound of the formula II having the thio group —S— is contacted with an oxidizing agent capable of transforming the thio group to a sulfinyl group

Exemplary oxidizing agents capable of such transformation include those recited for Reaction Scheme II, particularly an alkali metal metaperiodate such as sodium metaperiodate.

The oxidation is preferably conducted at a temperature of from about −50° C. to about +50° C.; most preferably from about 0° C. to about 30° C.; and preferably at a pressure of from about 1 atm to about 5 atm. The reaction is preferably completed over the course of about 1 hour to about 24 hours, and is preferably conducted under an atmosphere of inert gas such as argon.

Molar ratios of oxidizing agent to the starting compound of the formula II (n=0) are preferably about 1:1. Solvents are preferably employed which are selected from organic or inorganic solvents such as chloroform or methylene chloride, most preferably a mixture of methanol and water. Amounts of the solvent are preferably those where the formula II starting material is from about 1 to about 5% by weight, based on the combined weight of solvent and formula II compound.

The oxidizing method is novel.

Reaction Scheme VI
Method for the Preparation of
Compounds of the Formula II, n = 2

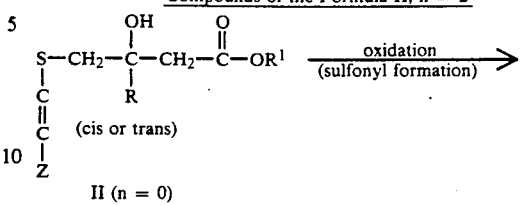

II (n = 0)

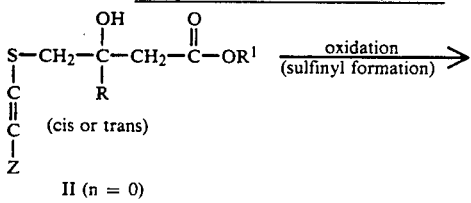

II (n = 1)

or

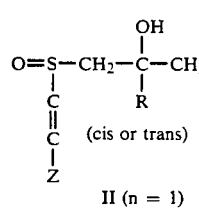

II (n = 1)

II (n = 2)

Compounds of the formula II where n is zero prepared as in Reaction Scheme IV above, or compounds of the formula II where n is 1 prepared as in Reaction Scheme V above, may be employed in Reaction Scheme VI for the preparation of compounds of the formula II where n is 2.

According to Reaction Scheme VI, a compound of the formula II having the thio group —S— or the sulfinyl group

is contacted with an oxidizing agent capable of transforming the thio or sulfinyl group to a sulfonyl group Exemplary oxidizing agents capable of such transformation include those recited for Reaction Scheme II. m-Chloroperoxybenzoic acid is preferred as the oxidizing agent.

The oxidation is preferably conducted at a temperature of from about 0° C. to about 100° C.; most preferably from about 30° C. to about 50° C.; and preferably at a pressure of from about 1 atm to about 5 atm. The reaction is preferably completed over the course of about 1 hour to about 24 hours.

Molar ratios of oxidizing agent to the compound of formula II where n=zero are preferably from about 2:1 to about 10:1, particularly from about 4:1 to about 6:1. Molar ratios of oxidizing agent to the compound of formula II where n=1 are preferably from about 1:1 to about 10:1, particularly from about 4:1 to about 6:1. Solvents are preferably employed which are selected from organic solvents such as methanol or methylene chloride, most preferably trichloromethane. Amounts of solvents are preferably those where the formula II starting material is from about 1 to about 5% by weight, based on the combined weight of solvent and formula II compound The oxidation method is novel.

The instant invention thus provides novel intermediates and methods of preparation which are described in the above Reaction Schemes. These novel intermediates include those compounds designated above as III, IV, and V, including all stereoisomers, salts and solvates thereof. Salts (and solvates by definition) thereof may be employed in, or prepared by, the novel methods of preparation wherever compounds of the formulae III, IV or V are employed or prepared.

The compounds of the invention may be prepared as racemic mixtures which may later be resolved, for example, to obtain the 3-S-isomer which is preferred. Preferably, optically active compounds of the invention are prepared directly by using chiral intermediates of the desired stereoisomeric configuration in the methods set forth in the above Reaction Schemes.

The compounds of the instant invention are inhibitors of 3-hydroxy-3-methylglutaryl coenzyme A (HMG-CoA) reductase and thus are useful in inhibiting cholesterol biosynthesis. The activity of the instant compounds therefor may be demonstrated by any of the tests set forth in British Patent No. 2,205,838, incorporated herein by reference. Generally, compound selectivity favoring greater inhibitory activity in hepatic tissue is an attribute for a cholesterol synthesis inhibitor.

The instant invention also provides pharmaceutical compositions comprising at least one of the inventive compounds in association with a pharmaceutically acceptable vehicle or diluent. The pharmaceutical composition may be formulated employing conventional solid or liquid vehicles or diluents, as well as pharmaceutical additives of a type appropriate to the mode of desired administration. The compounds may, for example, be administered by an oral route, such as in the form of tablets, capsules, granules or powders, or they may be administered by a parenteral route in the form of injectable preparations. Such dosage forms preferably contain from about 1 to 2000 mg of active compound per dosage. The dose to be administered depends on the unitary dose, the symptoms, and the age and the body weight of the patient, and may be determined by the skilled artisan. Exemplary pharmaceutical compositions of the instant invention are hypocholesterolemic, hypolipoproteinaemic, antiatheroschlerotic and/or hypolipidemic compositions comprising an amount of the inventive compound effective therefor.

The inventive compounds may be administered in a similar manner as known compounds suggested for use in inhibiting cholesterol biosynthesis, such as lovastatin, particularly to subjects which are mammalian species such as humans, dogs, cats and the like. Thus, the compounds of the invention may be administered in an amount from about 1 to 2000 mg in a single dose or in the form of individual doses from 1 to 4 times per day, preferably 4 to 200 mg in divided dosages of 1 to 100 mg, suitably 0.5 to 50 mg 2 to 4 times daily or in sustained release form.

The instant invention also provides methods for the treatment or prevention of hypercholesterolemia, atheroschlerosis, hyperlipoproteinaemia, and/or hyperlipidemia comprising the step of administering to a subject in need thereof an inventive compound in an amount effective therefor.

The following working Examples represent preferred embodiments of the present invention, and are not intended to limit the scope or spirit of the instant claims.

EXAMPLE 1

Preparation of (S)-4-[[[4'-Fluoro-3,3',5-trimethyl[1,1'-biphenyl]-2-yl]ethynyl]-thio]-3-hydroxybutanoic acid, methyl ester (a) 2,3,4-Trihydroxybutanoic acid, hydrated calcium salt

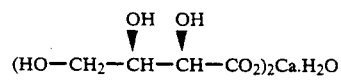

Calcium carbonate (50 g) was added to a solution of D-isoascorbic acid (44.0 g, 250 mM) in $H_2O$ (625 ml), and the suspension cooled to 0° C. (ice bath) and treated portionwise with 30% $H_2O_2$ (100 ml). The mixture was stirred at 30°-40° C. (oil bath) for 30 minutes. Darco (10 g) was added and the black suspension heated on a steam bath until evolution of $O_2$ ceased. The suspension was filtered through Celite, evaporated in vacuo (bath temperature 40° C.), taken up in $H_2O$ (50 ml), transferred to a large beaker and warmed on a steam bath. $CH_3OH$ was added until the solution was turbid and the beaker set aside in the fridge overnight. The gummy precipitated solid was collected by filtration, air dried overnight and ground in a mortar and pestle to give 30.836 g (75.2%) of the triol title product as a powdery white hydrated calcium salt with consistent $C^{13}$ NMR spectral data. TLC (7:2:1) isopropanol-$NH_4OH$—$H_2O$, Rf=0.19, PMA.

(b) 2,4-Dibromo-3-hydroxy butanoic acid, methyl ester

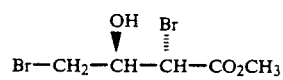

The triol obtained in step (a) above (30 g) was stirred in 30–32% HBr in acetic acid (210 ml) for 24 hours under Drierite. Methanol (990 ml) was then added to the brown solution and it was stirred overnight under Drierite. The mixture was evaporated to an orange oil, taken up in $CH_3OH$ (75 ml), refluxed for 2.0 hours, evaporated, partitioned between ethyl acetate (100 ml) and $H_2O$, the organic phase washed with $H_2O$ (2×) and brine, then dried over anhydrous $Na_2SO_4$ and evaporated to give 22.83 g (90.5%) of the dibromide title product as a light orange oil with consistent $C^{13}$ NMR spectral data. TLC (1:1) ethyl acetate-hexane, Rf=0.69, UV & PMA.

(c) (S)-4-Bromo-3-hydroxybutanoic acid, methyl ester

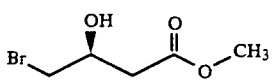

An argon purged solution of the dibromide obtained in step (b) above (20.8 g, 75.4 mM) and anhydrous sodium acetate (NaOAc) (21.0 g) in ethyl acetate (370 ml) and glacial acetic acid (37 ml) was treated with 5% Pd/C (1.30 g) and the black suspension stirred under one atmosphere of $H_2$ while monitoring uptake (22.4 l/mole). After 2.0 hours $H_2$ uptake was complete, the mixture was filtered through Celite, the filtrate washed with saturated NaHCO$_3$ and brine and then dried over anhydrous MgSO$_4$ and evaporated to give the crude bromoester title product as a brown oil. The crude oil was combined with another batch (starting from 36.77 g of the dibromide) and vacuum distilled to give 25.771 g (61.3%) of the pure bromoester title product as a clear oil with b.p.=79°-80° C. (1.0 mm Hg) and with consistent $C^{13}$ NMR spectral data. TLC (1:1) ethyl acetate-hexane, Rf=0.44, PMA.

Microanalysis is Calc'd for $C_5H_9O_3Br$: C, 30.48; H, 4.60; Br, 40.56
Found: C, 29.76; H, 4.50; Br, 39.86.

(d) Methyl 3S-((t-butyl)diphenylsilyloxy)-4-bromo butanoate

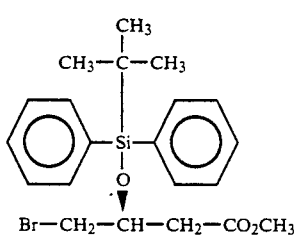

A solution of (S)-4-bromo-3-hydroxybutanoic acid, methyl ester obtained in step (c) above (4.0 g, 20.4 mmole), imidazole (6.94 g, 5.0 eq.), and 4-dimethylamino pyridine (4-DMAP) (12 mg, 0.005 eq.) in dry dimethylformamide (DMF) (40 ml) was treated with t-butyldiphenylsilyl chloride (5.84 ml, 1.1 eq.) and the homogeneous mixture stirred overnight under argon at room temperature. The mixture was partitioned between 5% KHSO$_4$ and ethyl acetate, the organic phase washed with H$_2$O and brine then dried over anhydrous Na$_2$SO$_4$ and evaporated to give 9.32 g (100%) of the title compound as a clear, viscous oil with consistent $C^{13}$ NMR spectral data. TLC (3:1) hexane-ethyl acetate, product. Rf silyl ether=0.75, U. V. and PMA.

(e) Methyl 3S-((t-butyl)diphenylsilyloxy)4-iodo butanoate

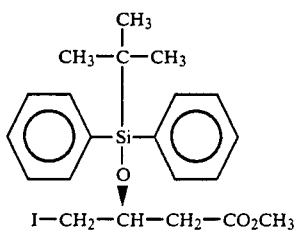

A solution of the crude methyl 3S-((t-butyl)-diphenylsilyloxy)-4-bromo butanoate obtained in step (d) above (9.32 g, 201 mmole) in methyl ethyl ketone (60 ml, over 4Å sieves) was treated with sodium iodide (15.06 g, 100.5 mmole, 5.0 eq.) and the yellow suspension refluxed for 5.0 hours under argon. The mixture was cooled, diluted with ethyl acetate, filtered, the filtrate washed with dilute NaHSO$_3$ (until colorless) and brine, then dried over anhydrous Na$_2$SO$_4$ and evaporated in vacuo to give 10.17 g of a yellow oil. The crude oil was purified by flash chromatography on Merck silica gel (600 g, 50:1) eluting with (3:1) hexane-CH$_2$Cl$_2$. Product fractions were evaporated to give 7.691 g (74.2%, combined yield for both steps) of the title compound as a clear, colorless, viscous oil with consistent $C^{13}$ NMR spectral data and $H^1$ NMR spectral data. TLC (3:1) hexane-ethyl acetate, product. Rf=0.75, U.V. and PMA. (Product co-spots with starting material).

(f) Methyl 3S-t-butyldiphenylsilyloxy-4-thiotosylate butanoate

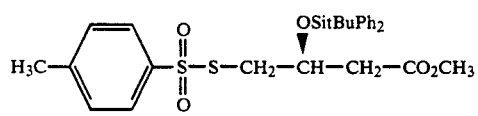

A reaction mixture containing potassium thiotosylate (2.2 g, 10 mM), and methyl 3S-((t-butyl)diphenylsilyloxy)-4-iodo butanoate obtained in step (e) above (4.9 g, 10 mM) in dimethylformamide (25 ml) was stirred at room temperature for 3 days and heated at 50° C. for 24 hours until thin layer chromatography (TLC) indicated an absence of starting material. The reaction mixture was diluted with ethyl acetate (EtOAc) (200 ml), washed 2×saturated NaHCO$_3$, 1×H$_2$O, 1×saturated NaCl, dried (Na$_2$SO$_4$) and concentrated under reduced pressure. The oily residue was purified by flash chromatography (Merck Silica gel, 10% EtOAc/Hexane), yielding the pure title product as a colorless oil (5.32 g, 98.0%).

Anal. Calc'd for $C_{28}H_{24}S_2SiO_5$
Calc'd C,61.96; H,6.31; S, 11.81;
Found C,61.71; H,6.37; S, 11.64.

(g) 2,4-Dimethyl-N-phenylbenzenemethanimine

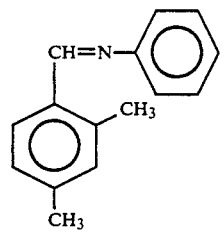

A solution of freshly distilled 2,4-dimethylbenzaldehyde (6.97 ml, 50 mmole) and distilled aniline (4.56 ml, 50 mmole) in dry toluene (80.0 ml) was refluxed for 3.0 hours under argon in a flask equipped with a Dean-Stark apparatus. The mixture was cooled, then evaporated in vacuo to a yellow oil. The crude oil was purified by Kugelrohr distillation (0.5 mm Hg, 160°-180° C.) to give 8.172 g (78.1%) of the title benzeneimine as a light yellow oil which crystalized on standing to a low melting solid. H¹ NMR was consistent for the title product. TLC (4:1) Hexane-Acetone, Rf=0.67 and 0.77 (geometric isomers), U.V. and I₂.

(h) 2,4-Dimethyl-N-phenylbenzenemethanimine, dipalladium acetate complex

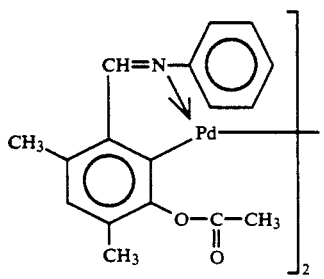

A mixture of the benzeneimine prepared in step (g) above (6.0 g, 28.6 mmole) in glacial acetic acid (144 ml) was treated with palladium(II)acetate (6.44 g, 28.7 mmole) and the clear, red homogeneous solution refluxed under argon for one hour. The resulting turbid mixture was filtered warm through a packed ½" bed of Celite into 900 ml of H₂O. Precipitated orange solid was collected by filtration and dried in vacuo at 65° C. over P₂O₅ for 16.0 hours to give 10.627 g (85.5%) of the title palladium complex as an orange solid with m.p.=194°–196° C. (Literature m.p. of a recrystallized analytical sample=203°–205° C.).

(i) 4'-Fluoro-3,3', 5-trimethyl-2-formyl-1,1'-biphenyl

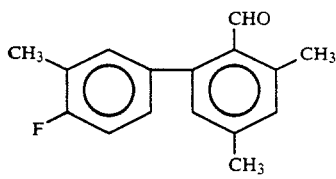

A Grignard reagent having the structure:

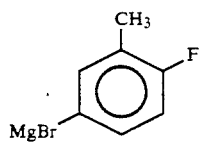

was prepared by adding 5-bromo-2-fluorotoluene (22.5 g, 60.9 mmole) portionwise (enough to keep the (C₂H₅)₂O continually refluxing) to stirred magnesium turnings (1.35 g, 55.4 mmole, 8.0 eq.) in dry (C₂H₅)₂O (70.0 ml). The reaction was initiated in an ultrasound device. After bromide addition was complete, the mixture was stirred for one hour under argon at room temperature, then refluxed for 15 minutes and finally cooled back to room temperature.

In a second flask, a mixture of the dipalladium complex obtained in step (h) above (3.0 g, 6.92 mmole) and triphenylphosphine (14.52 g, 55.4 mmole, 8.0 eq.) in dry benzene (100 ml) was stirred at room temperature under argon for 30.0 minutes. The freshly prepared and filtered (glass wool plug) Grignard reagent was then added in one portion by means of a cannula to this solution and the mixture was stirred for 1.5 hours at room temperature under argon. 6.0N HCl (35 ml) was added, the mixture stirred an additional hour at room temperature, then filtered through packed Celite (½" bed). The filtrate was diluted with (C₂H₅)₂O (250 ml), washed with brine (2×100 ml), dried over anhydrous MgSO₄ and evaporated in vacuo to give 13.35 g of a viscous orange oil which crystallized on standing. The crude orange solid was purified by flash chromatography on Merck silica gel (700 g) eluting with neat hexane, followed by (95:5) hexane-(C₂H₅)₂O. Product fractions were evaporated to give 1.507 g (89.9%) of the title aldehyde as a light yellow solid with m.p.=72°–75° C. (Literature reports m.p.=73°–74° C.).

TLC: (95:5) hexane-(C₂H₅)₂O, Rf=0.40, U.V. and PMA.

(j) 4'-Fluoro-3,3',5-trimethyl-2-(2,2-dibromovinyl)-1,1'-biphenyl

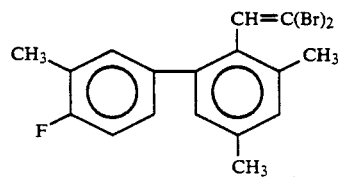

A cooled (−10° C., salt/ice bath) solution of the biphenyl aldehyde prepared in step (i) above (242 mg, 1.0 mmole) and triphenylphosphine (787 mg, 3.0 mmole, 3.0 eq) in dry CH₂Cl₂ (10 ml) was treated dropwise with a CBr₄ solution (497 mg, 1.5 mmole, 1.5 eq in CH₂Cl₂ (5.0 ml)) over a 5 minute period. After 30 minutes at 0° C. the red-orange solution was partitioned between CH₂Cl₂ and saturated NaHCO₃. The organic phase was washed with saturated NaHCO₃ and brine, then dried over anhydrous Na₂SO₄ and evaporated to give 1.478 g of a light brown solid. The crude solid was purified by flash chromatography on LPS-1 silica gel (50:1) eluting with (9:1) hexane-CH₂Cl₂. Product fractions were evaporated to give 392 mg (99%) of the pure vinyl dibromide title product as a pale yellow oil with consistent ¹H-NMR and ¹³C-NMR spectral data. TLC (95:5) hexane-ethyl acetate, Rf=0.51, UV and PMA. Mass spec, M+H=399 observed.

(k) 4'-Fluoro-3,3',5-trimethyl-2-ethynyl-1,1'-biphenyl

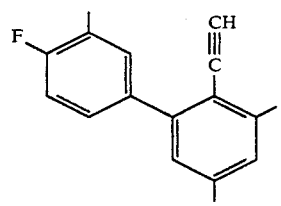

A −78° C. (dry ice/acetone) solution of the vinyl dibromide prepared in step (J) above (336 mg, 0.844 mmole) in dry tetrahydrofuran (5 ml) was treated dropwise via syringe with a 1.6M solution of n-butyl lithium (n-BuLi) in hexanes (1.06 ml, 1.7 mmole, 2.0 eq) and the mixture stirred at −78° C. under argon for one hour. During the n-BuLi addition color changes from colorless to deep yellow to pale yellow to deep-blue purple were evident. The mixture was quenched at −78° C. by the dropwise addition of saturated NH₄Cl (4 ml), allowed to warm to room temperature, extracted with ($C_2H_5)_2O$, the ethereal layer washed with brine, dried over anhydrous $MgSO_4$ and evaporated to give 191 mg of a green oil. The crude oil was purified by flash chromatography on LPS-1 silica gel (60:1) eluting with neat hexanes. Product fractions were evaporated to give 185 mg (92%) of the title acetylene product as a clear oil which eventually turned deep blue on standing at −20° C. under argon. $^1$H-NMR and $^{13}$C-NMR were consistent for the title product. TLC neat hexane, Rf=0.18 UV (bright purple) and PMA. Mass Spec. M+H=239 observed.

(l)
(S)-4-[[[4'-Fluoro-3,3',5-trimethyl-[1,1'-biphenyl]-2-yl]ethynyl]thio]-3-(t-butyldiphenylsilyloxy)butanoic acid, methyl ester

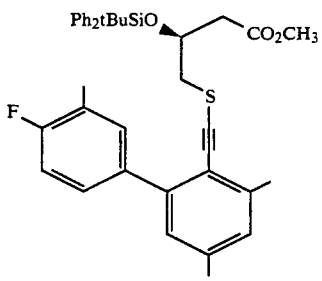

A −78° C. solution of the acetylene compound prepared in step (k) above (1.10 g, 4.65 mM) in dry tetrahydrofuran (20 ml) was treated dropwise with a 2.5M solution of n-butyl lithium in hexanes (1.86 ml, 4.65 mM, 1.0 eq). The mixture was stirred under argon for 30 minutes and then transferred via canula to a −78° C. solution of methyl 3S-t-butyldiphenylsilyloxy-4-thiotosylate butanoate prepared in step (f) above in dry tetrahydrofuran (20 ml). The clear pale yellow reaction mixture was stirred at −78° C. for 2 hours and then slowly warmed to room temperature. The reaction mixture was quenched with saturated $NH_4Cl$, and extracted with ether. The ethereal layer was washed with saturated $NaHCO_3$ and brine, then dried over anhydrous $MgSO_4$ and evaporated to a brown oily residue. Purification by flash chromatography (Merck Silica gel, 3% ethyl acetate/hexane) afforded the title product as a colorless oil (2.42 g, 83.7%).

(m)
(S)-4-[[[4'-Fluoro-3,3',5-trimethyl[1,1'-biphenyl]-2-yl]ethynyl]thio]-3-hydroxybutanoic acid, methyl ester

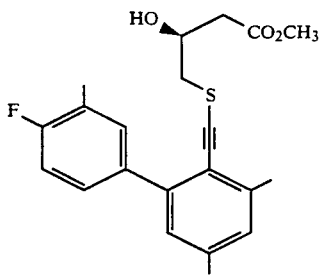

A solution of (S)-4-[[[4'-fluoro-3,3',5-trimethyl[1,1'-biphenyl]-2-yl]ethynyl]thio]-3-(t-butyldiphenylsilyloxy)butanoic acid, methyl ester (1.2 g, 1.9 mM) in dry tetrahydrofuran (10 ml) was treated with glacial acetic acid (0.43 ml, 7.70 mM, 4.0 eq) followed by a 1.0M tetrabutylammonium fluoride solution in tetrahydrofuran (5.78 ml, 5.78 mM, 3.0 eq) and the dark reaction mixture stirred overnight at room temperature under argon. The mixture was diluted with 10 ml of ice water and extracted with ethyl acetate (2×). The organic phase was washed with saturated $NaHCO_3$ and brine, then dried over anhydrous $Na_2SO_4$ and evaporated to give a dark oily residue. The crude oil was purified by flash chromatography (Merck Silica gel, 20% ethyl acetate/hexane) affording the title compound as a dark oil (0.53 g, 71.6%).

EXAMPLE 2

Preparation of
(S)-4-[[[4'-Fluoro-3,3',5-trimethyl[1,1'-biphenyl]-2-yl]ethynyl]thio]-3-hydroxybutanoic acid, monosodium salt

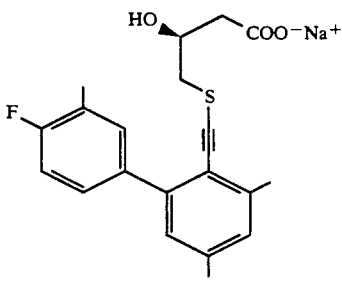

A solution of (S)-4-[[[4'-fluoro-3,3', 5-trimethyl[1,1'-biphenyl]-2-yl]ethynyl]thio]-3-hydroxybutanoic acid, methyl ester obtained in Example 1 above (0.15 g, 0.39 mM) in methanol/$H_2O$ (3/1) was treated with 1N NaOH (1.16 ml, 1.16 mM, 3 eq) and stirred at room temperature for 1 hour (TLC indicated the absence of starting material). The reaction mixture was concentrated and the residue dissolved in a minimum amount of water and chromatographed on HP-20 resin eluting with $H_2O$ until neutral fractions were obtained, followed by 25% methanol/$H_2O$, 50% methanol/$H_2O$ and 75% methanol/$H_2O$. Collected product fractions were evaporated, dissolved in $H_2O$, filtered, frozen and lyophilized to a white lyophilate as the title compound sodium salt (115 mg, 86.0%).

$R_f$=0.24 (EM Silica gel) 20% $CH_3OH/CHCl_3$, UV,$I_2$ UV λ max (ε)=240 (26,020), 207 nm (30,840) Anal. Calc'd for $C_{21}H_{20}FO_3SNa \times 0.66\ H_2O$. Calc'd C,62.09; H,5.29; F,4.68; S,7.89. Found C,62.11; H,5.08; F,4.78; S,7.70.

EXAMPLE 3

Preparation of (S)-4-[[[4'-Fluoro-3,3',5-trimethyl[1,1'-biphenyl]-2-yl]ethynyl]sulfinyl]-3-hydroxy-butanoic acid, monosodium salt

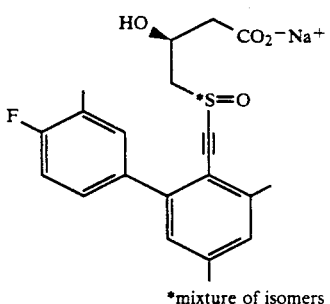

*mixture of isomers

A solution of (S)-4-[[[4'-fluoro-3,3',5-trimethyl[1,1'-biphenyl]-2-yl]ethynyl]thio]-3-hydroxybutanoic acid, monosodium salt (175 mg, 0.44 mM) prepared as in Example 2 above and sodium metaperiodate (0.56 g, 2.64 mM) in $CH_3OH/H_2O$ (6 ml, 1/1) was stirred under argon for 24 hours. (TLC indicated the absence of starting material). The reaction mixture was concentrated, the residue dissolved in a minimum amount of water and chromatographed on HP-20 resin eluting with $H_2O$, followed by 25% $CH_3OH/H_2O$, 50$CH_3OH/H_2O$ and 75% $CH_3OH/H_2O$. Collected product fractions were evaporated, dissolved in $H_2O$ (50 ml), filtered, frozen and lyophilized to a white electrostatic lyophilate as the title compound sodium salt (133 mg, 73.8 %) (mixture of sulfoxide isomers). $R_f$=0.40 (EM Silica gel) 30% $CH_3OH/CHCl_3$, UV,$I_2$ UV λ max (ε)=273 (14,300), 238 (27,800), 209 nm (33,300)

Anal. Calc'd for $C_{21}H_{20}FO_4SNa \times 2.40\ H_2O$.
Calc'd C,55.60; H,5.51; F,4.19; S,7.07.
Found C,55.16; H,5.03; F,3.99; S,6.61.

EXAMPLE 4

Preparation of (S)-4-[[[4'-Fluoro-3,3',5-trimethyl[1,1'-biphenyl]-2-yl]ethynyl]sulfonyl]-3-hydroxybutanoic acid, monosodium salt

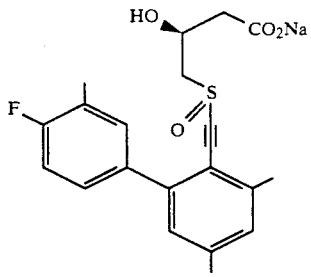

A reaction mixture containing (S)-4-[[[4'-fluoro-3,3',5-trimethyl[1,1'-biphenyl]-2-yl]-ethynyl]thio]-3-hydroxybutanoic acid, monosodium salt prepared in Example 2 above (0.17 g, 0.43 mM) and m-chloroperoxybenzoic acid (0.178 g, 0.86 mM, 80–85%) in $CHCl_3$ (10 ml) was stirred at room temperature for 24 hours (TLC indicated the absence of starting material). The reaction mixture was concentrated, the residue dissolved in water and chromatographed on HP-20 resin eluting with $H_2O$, followed by 25% $CH_3OH/H_2O$, 50% $CH_3OH/H_2O$ and 75% $CH_3OH/H_2O$. Collected product fractions were evaporated, dissolved in $H_2O$ (100 ml, milky solution), frozen and lyophilized to an off-white residue, which was triturated with hexane yielding off-white hard solids of the title product, (0.15 g, 55.5%)

$R_f$=0.50 (EM Silica gel) 30% $CH_3OH/CHCl_3$, UV,$I_2$ UV λ max (ε)=274 (13,800), 236 (16,500), 205 nm (35,900)

Anal. Calc'd for $C_{21}H_{20}FO_5SNa \times 0.25\ C_6H_{14}$.
Calc'd C,60.33; H,5.29; F,4.24; S,7.16.
Found C,60.54; H,5.00; F,4.07; S,7.35.

What is claimed is:

1. A compound having the following formula I or II:

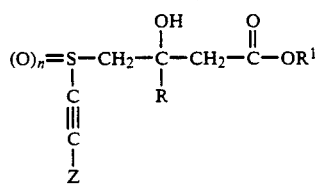

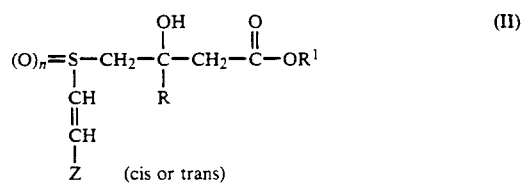

where:

n is 0, 1 or 2;

R is hydrogen or lower alkyl;

Z is a substituted or unsubstituted biphenyl group; and $R^1$ is hydrogen, alkyl or aryl; or a salt thereof.

2. A compound of claim 1, wherein said salt is a pharmaceutically acceptable salt.

3. A compound of claim 1, wherein the chiral center

of the sulfur-containing side chain of said compound is of the same absolute configuration corresponding to when R=hydrogen and —OH is of the S configuration.

4. A compound of claim 1 of the formula I or a salt thereof.

5. A compound of claim 1, where R is hydrogen.

6. A compound of claim 1, where $R^1$ is hydrogen or an alkali metal cation.

7. A compound of claim 1, where Z is a lipophilic anchor group which is capable of binding to a hydrophobic part of HMG-CoA reductase not utilized in binding HMG-CoA.

8. A compound of claim 1 wherein Z is selected from a substituted or unsubstituted biphenyl where

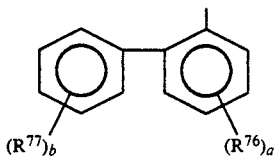

a is 1, 2, 3, or 4 and each $R^{76}$ substituent is independently selected from
(i) hydrogen,
(ii) alkyl,
(iii) aryl,
(iv) aralkyl,
(v) aralkoxy,
(vi) heterocyclo,
(vii) cycloalkyl,
(viii) alkoxy,
(ix) alkenyl,
(x) cycolalkenyl,
(xi) halogen,
(xii) hydroxy,
(xiii) amino,
(xiv) alkylamino, or
(xv) dialkylamino; and b is 1, 2, 3, 4, or 5 and each $R^{77}$ substituent is independently selected form those groups (i) to (xv) described above for $R^{76}$.

9. A compound selected from the group consisting of:
(S)-4-[[[4'-fluoro-3,3',5-trimethyl[1,1'-biphenyl]-2-yl]ethynyl]thio]-3-hydroxybutanoic acid, methyl ester;
(S)-4-[[[4'-fluoro-3,3',5-trimethyl[1,1'-biphenyl]-2-yl]ethynyl]thio]-3-hydroxybutanoic acid;
(S)-4-[[[4'-fluoro-3,3',5-trimethyl[1,1'-biphenyl]-2-yl]ethynyl]sulfonyl]-3-hydroxybutanoic acid; and
(S) 4-[[[4'-fluoro-3,3',5-trimethyl[1,1'-biphenyl]-2-yl]ethynyl]sulfinyl]-3-hydroxybutanoic acid.

10. A hypocholesterolemic composition comprising an amount of said compound of claim 1 effective therefor, and a pharmaceutically acceptable vehicle or diluent.

11. A hypolipidemic composition comprising an amount of said compound of claim 1 effective therefor, and a pharmaceutically acceptable vehicle or diluent.

12. A hypoliproteinaemic composition comprising an amount of said compound of claim 1 effective therefor, and a pharmaceutically acceptable vehicle or diluent.

13. An antiatheroschlerotic composition comprising an amount of said compound of claim 1 effective therefor, and a pharmaceutically acceptable vehicle or diluent.

* * * * *